United States Patent [19]
Pira

[11] Patent Number: 6,017,337
[45] Date of Patent: Jan. 25, 2000

[54] CRYOPROBE BASED ON A PELTIER MODULE

[76] Inventor: Luc Pira, Vestinglaan 51., B-2640 Mortsel, Belgium

[21] Appl. No.: 08/963,921

[22] Filed: Nov. 4, 1997

[30] Foreign Application Priority Data

Nov. 4, 1996 [BE] Belgium ................................ 09600928

[51] Int. Cl.$^7$ ...................................................... A61N 5/00
[52] U.S. Cl. ................................. 606/20; 607/96; 606/23; 601/15
[58] Field of Search ................................ 607/96, 98, 104, 607/113; 606/20–23, 27; 601/15

[56] References Cited

U.S. PATENT DOCUMENTS

| | | | |
|---|---|---|---|
| 3,133,539 | 5/1964 | Eduis | 128/399 |
| 3,168,895 | 2/1965 | Okuhara | 128/399 |
| 3,451,904 | 6/1969 | Boehmer et al. | |
| 3,971,229 | 7/1976 | Privas . | |
| 4,585,002 | 4/1986 | Kissin | 128/399 |
| 4,640,284 | 2/1987 | Ruderian | 128/399 |
| 4,657,531 | 4/1987 | Choi | 607/96 |
| 4,860,748 | 8/1989 | Chiurco et al. | 128/399 |
| 4,915,108 | 4/1990 | Sun | 128/402 |
| 5,097,828 | 3/1992 | Deutsch | 128/399 |
| 5,198,752 | 3/1993 | Miyata et al. | 324/158 F |
| 5,207,674 | 5/1993 | Hamilton . | |
| 5,314,423 | 5/1994 | Seney | 606/20 |

FOREIGN PATENT DOCUMENTS

| | | |
|---|---|---|
| 0 239 048 | 9/1987 | European Pat. Off. . |
| 1262927 | 9/1961 | France . |
| 2 613 611 | 10/1988 | France . |
| 1 126 426 | 3/1962 | Germany . |
| 33 09 093 | 9/1984 | Germany . |
| 93 06 669 U | 8/1993 | Germany . |
| 2 286 660 | 8/1995 | United Kingdom . |
| WO 93/16667 | 9/1993 | WIPO . |

Primary Examiner—Cary O'Connor
Assistant Examiner—Michael Astorino
Attorney, Agent, or Firm—Schmeiser, Olsen & Watts

[57] ABSTRACT

An apparatus is described which is suitable for thermal treatment of the human or animal skin and underlying tissue, substituting ice frictions, and cold sprays. This cryoprobe is characterised by a Peltier module with a cold and a hot side. An electrical power supply drives the Peltier module. The cold side is mounted at a cooling head, by which the skin is treated, whereas the hot side is cooled by a heat dissipation element which is itself cooled by a cooling fluid. A temperature sensor in the cooling head allows to control the temperature of treatment. The cryoprobe may be controlled by a micro-controller or by a personal computer.

20 Claims, 12 Drawing Sheets

CRYOPROBE BASED ON A PELTIER MODULE

FIELD OF THE INVENTION

This invention relates to an apparatus referred to as "cryoprobe" or "cooling probe" for cooling or heating of a flexible surface. More specifically, this apparatus can be used for thermal treatment of the skin of the human or an animal body.

The main purpose of the cryoprobe is to replace traditional ice cubes and other cooling media. Although thermal therapy is also possible, the cryoprobe will mainly be applied by physio-therapists and in general medicine. Cooling is a good therapy and an approved method against specific inflammations, which is known for several centuries.

In comparison with existing means, our cryoprobe has the advantage that temperature, power and cooling time are controllable. The cryoprobe according to the current invention can be designed in a good manipulable hand probe, see FIG. 13, which shows a three-dimensional model. The cryoprobe has an enormous large cooling power.

BACKGROUND OF THE INVENTION specific diseases require a local treatment of the skin by cold or heat, or a treatment under controlled temperature variations with a big cooling power. Because the main purpose of the probe is to cool, we will discuss mainly the cooling aspect. Cold is up to now one of the oldest and most frequently used means in the treatment of acute musculoskeletal injuries. It gives, according to various authors, the following advantageous effects:

1) Increase of blood circulation (Travell, J., Simons, D.: Myofascial Pain and Dysfunction, The Trigger point manual, volume 1 & 2, Williams and Wilkins)
2) Increase of articular mobility (Nielson, A. J.: Spray and stretch for relief of myofascial pain. Physical Therapy, 58, 567–569, 1978)
3) Diminish inflammation (Schmidt, K. L., e.a.; Heat, cold and inflammation, Zeitschrift für Rheumatologie, 38, 391–404, 1979)
4) Diminish oedema (Meeusen R. e.a.: Cryotherapy in sportmedicine—the effect of topical ice application on the permeability of the lymphvessels, Sports and Medicine, McGregorand Moncur, 246–250, 1986)
5) Increase of muscular relaxation (Clenendi, N. M. A. and Czumski, A. J.: Influence of cutaneous ice application on single motor units in humans. Physical Therapy, 51, 166–175, 1971)
6) Diminish muscular spasms (6) (Lee, J. M. and Warren, M. P.: Cold Therapy in rehabilitation, Belt & Hymen, London 19978)
7) Diminish pain (Grant, A. E.: Massage with ice in the treatment of painful conditions of the musculoskeletal system, Arch. Phys. Med. Rehab., 44, 233–238, 1964)
8) Breaking the pain and spasm cycle (8) (Oison, J. E. and Stravino, V. D.: A review of cryotherapy. Physical Therapy, 53, 53, 840–853, 1972)

In the past, cold therapy or cryotherapy has often been applied by means of ice cubes, within or without a housing, e.g. a waterproof pocket or a cup. At the same time, pockets containing a specific gel were offered for sale. These were cooled in a cooling space. Thereafter, they were applied to the skin. Alternatively, cold air was blown, via a cooling system, on the skin of a part of the body. Another method is the application of very volatile substances having a low boiling point, such as ethylchloride and/or fluorimethane. These are CPKs and are harmful for ozone and poisonous for human beings. Their use has been forbidden in certain states of the USA due to these reasons.

All above mentioned systems have the problem that temperature control of the cooling medium and the treated surface is very poor, or even impossible. Also the cooling power by other media is too low to be therapeutically significant.

The problem is thus to develop a system by which the heat production or heat dissipation can be controlled continuously and by a sufficient power. This allows to substitute ice and has the advantage that it may be designed in a handy form for use, see FIG. 13).

U.S. Pat. No. 4,519,389 describes a cryoprobe for freezing the eye-lens during surgery. This cryoprobe consists of a small Peltier element. The cold side is in direct contact with the eye-lens. The hot side is mounted on a heat dissipating element, which may be used as an electrical conductor. The heat dissipating element is cooled by the environmental atmosphere or by contacting the hand of the physician.

Although this type of cryoprobe is suitable for cooling small surfaces, such as an eye-lens, it is not suited for cooling larger bodies such as good circulated skin, musculi and other underlying tissues.

On the one hand it is impossible for one Peltier element, mounted this way, to provide the required heat transport. On the other hand it is impossible that this amount of heat, released by the part of the body, can be dissipated by the environmental air, unless its flow is substantially forced. At the same time, the heat that is removed, must be conducted suitably through the cryoprobe, such that the environment does not unwantedly undo a portion of the useful heat transport.

Also in the patent U.S. Pat. No. 3,207,159, U.S. Pat. No. 4,585,002, U.S. Pat. No. 4,860,748, U.S. Pat. No. 3,133,539, U.S. Pat. No. 3,168,895, U.S. Pat. No. 4,915,108, EP-A-0 552 379 and EP-A-0 651 308, Peltier elements are used to cool the skin. However, none of the embodiments therein have a useful cooling capacity comparable to the capacity of ice frictions.

OBJECTS OF THE INVENTION

The object of the present invention is to provide a cryoprobe or cooling probe comprising a Peltier element or module, that produces a sufficiently large cooling power, with preferably 30 Watt pumping power at 9 $cm^2$.

It is another object of the invention that the efficiency of the cryoprobe is comparable to the use of ice or other media, used for this application.

It is yet another object of the invention that the cryoprobe is easy to handle and comes in a user-friendly form.

Another object is to elaborate a novel technique for fastening a Peltier module, thereby achieving an optimal heat transport:
  from the cold side of the Peltier module to the cooling head; and,
  from the hot side of the Peltier module to the heat dissipating element.

Another object of the invention is to control and drive the temperature of the cryoprobe, in order to save the lifetime of the Peltier module.

Another object of the invention is to make the cryoprobe suitable for application on resilient surfaces.

Further objects and advantages of the present invention will be disclosed and become apparent from the following description.

SUMMARY OF THE INVENTION

The current invention relates to a cryoprobe or cooling probe including the features set out in claim 1. More specific features for preferred embodiments are set out in the dependent claims.

By use of a Peltier module, as described further in detail, more heat can be dissipated than with one Peltier element. In the text below, Peltier element or Peltier module will be used interchangeably, always referring to a Peltier module. It is preferred to design a cooling head such that it takes the desired form of the surface to be cooled.

For cold therapy of skin surfaces, it is preferred that this cooling heat has the form of a truncated cone or is conic. This form increases the continuous transport of heat from the basis of the cone, where the Peltier element is located, to the top, where the surface to be cooled is located. The upper portion of this cone, which is in contact with the skin, is preferably slightly spherical. The outer surface of the conic form of the cooling head is preferably isolated by an insulating synthetic housing, from the top to the bottom. A temperature sensor in the cooling head enables temperature control of the cooling head, by means of the necessary electronics, such that the appropriate correct electronic actions can be executed when the temperature reaches an undesired value. A heat dissipating element or cooling rib enables to dissipate the heat generated at the hot side of the Peltier module. The thermally conductive fluid, in contact with the heat dissipating element, provides a good dissipation of heat, without too much noise. High-pressure air might be used for heat dissipation, but it appears to be less suitable than fluids with a high caloric absorption, such as ethylglycol with water.

DETAILED DESCRIPTION OF THE INVENTION

The invention is hereinafter disclosed by an examples, referring to the accompanying figures, wherein:

FIG. 14b shows the lower housing corresponding with FIG. 14a.

Figure 1:
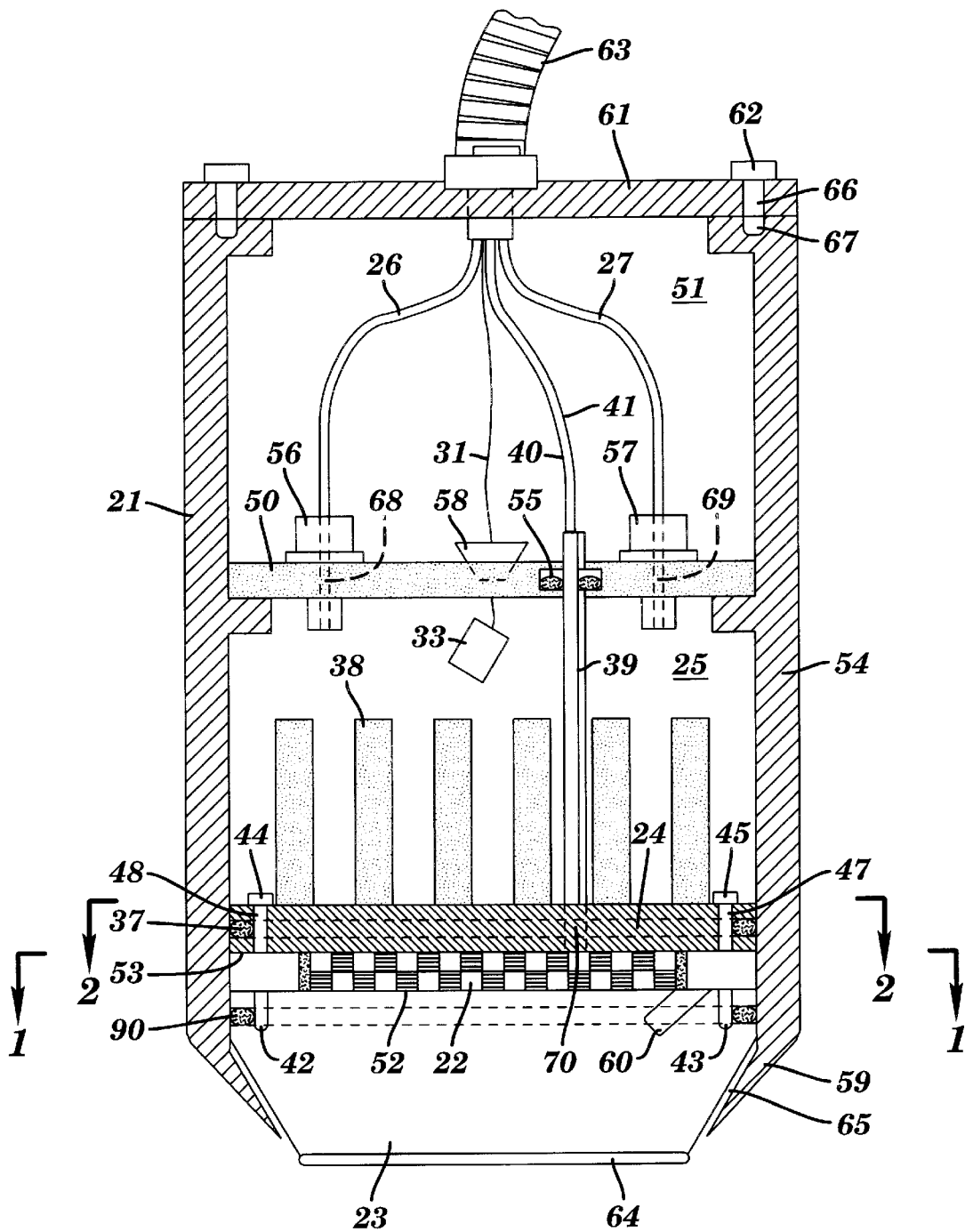
FIG. 1 is a cross-section of the cryoprobe according to the current invention.

FIG. 1 shows schematically a cross-section of the cryoprobe according to the current invention, with essential parts as set out in claim 1. One embodiment for the cryoprobe is now described in conjunction with FIGS. 1, 14a, 14b, 15a, 15b, 16a and 16b. Equal reference numbers indicate equal elements on the different figures.

Figure 14A:
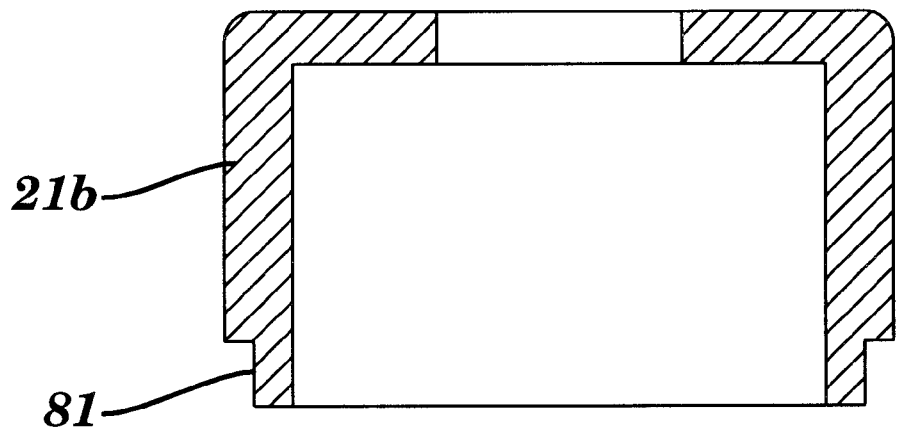
FIG. 14a shows the upper housing of a specific cryoprobe.
Figure 14B:
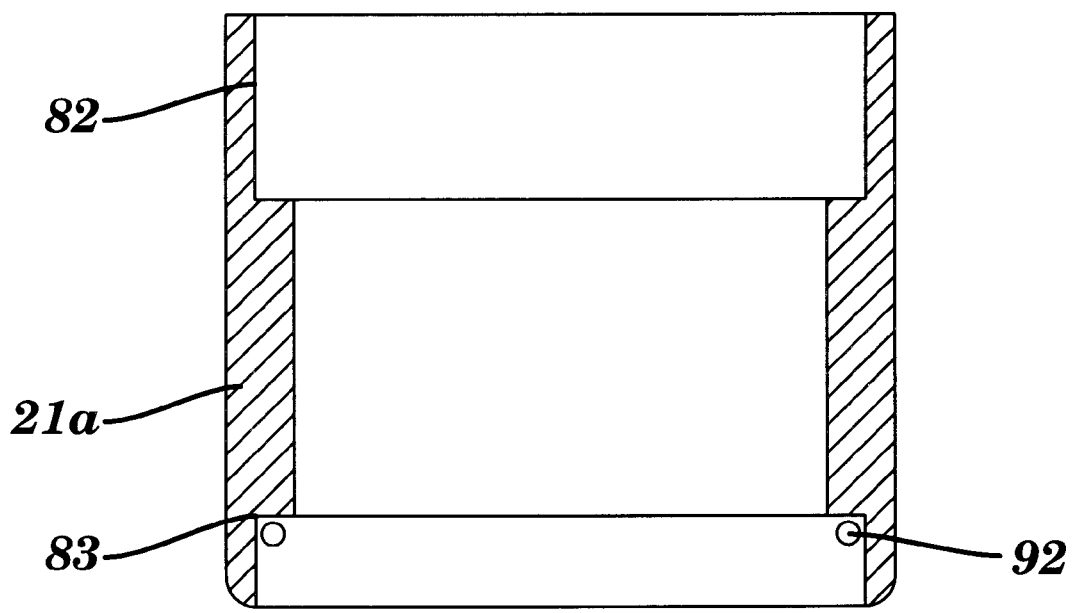

The housing 21, schematically represented on FIG. 1, is represented in more detail in FIG. 14a and 14b. The housing 21 comprises lower housing 21a and upper housing 21b. The upper housing 21b has a narrow portion 81 of the outer surface, which fits exactly in a wider portion 82 of the inner surface of the lower housing 21a. During assembly, both are mounted and fitted together. The lower housing has a wider section below than e.g. in the middle, such that a flange 83 is formed.

Figure 15A:
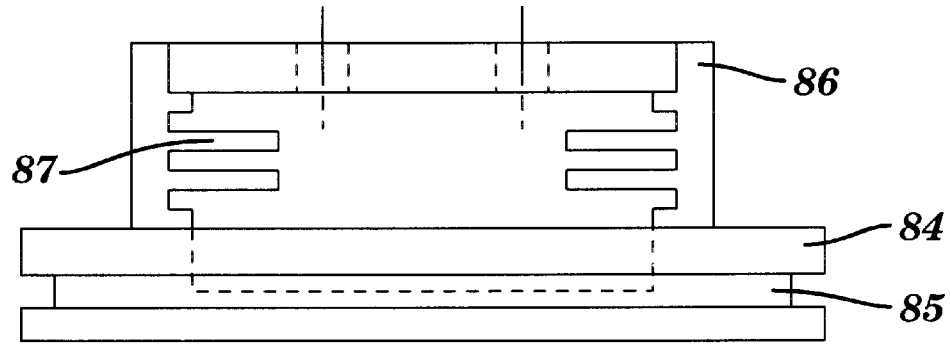
FIG. 15a shows a side view of the lower part of a heat dissipation element.
Figure 15B:
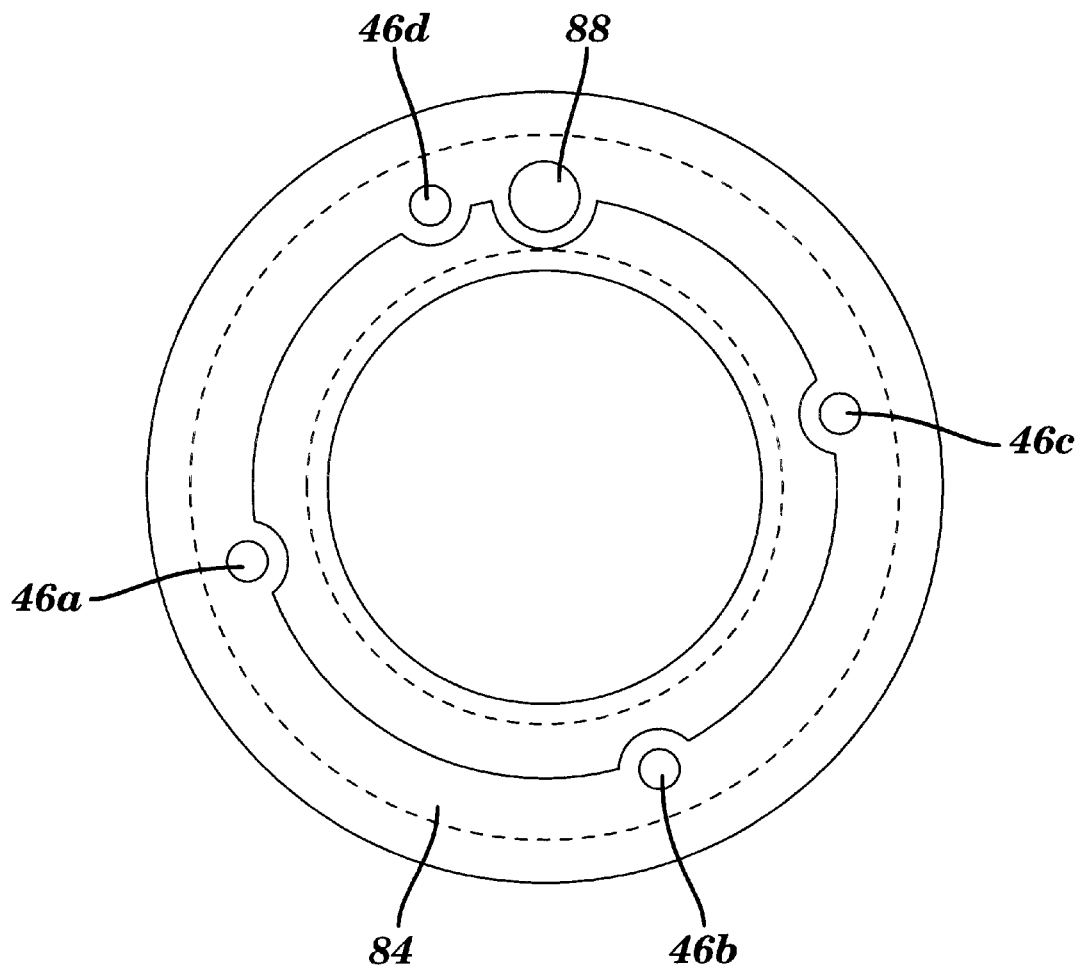
FIG. 15b shows a top view of the upper part of the heat dissipation element.

FIG. 15a and FIG. 15b show a heat dissipation element 24. This element is preferably made copper, since the heat transport of copper is three times better than the heat transport of aluminum. Due to improved heat dissipation, the temperature of the hot junction will be lower. As such, the efficiency of the Peltier module will improve dramatically. All copper parts are covered preferably by a thin layer of silver. The silver is preferably passivated, to avoid oxidation of copper and silver. The heat dissipation element comprises a lower circular disc 84, having a diameter of 44.8 mm and a thickness of 6.5 mm. In the cylindrical outer surface of the disc 84, a groove is provided, having a depth of 2 mm and being 1.5 mm wide. In this groove, an O-ring 37 (see FIG. 1) for sealing off cooling fluid may be fitted. On the disc 84, a cup 86 is mounted. The outer surface of the cup is cylindrical, the inner surface shows large circular cooling fins 87. The cup is sealed on the upper side by a lid (not shown), having two tubes: one to supply and one to drain the cooling fluid. it is important that the outlets of the tubes are situated on a different level in the cup, to avoid immediate drain of the supplied cooling fluid. A better efficiency was obtained when the cooling fluid was supplied by the lower positioned inlet within the cup and was drained by the upper outlet within the cup. Also the lid of the cup is preferably made of copper, and is soldered on the cup during manufacturing. As such, the whole heat dissipation element forms a closed heat-circuit, which improves considerably the heat transport. In the lower circular disc 84 are provided four holes 46a, 46b, 46c and 46d, to pass screws, which is further described hereinbelow. Moreover, one opening 88 is provided for passing the conductors of a heat sensor.

Figure 16A:
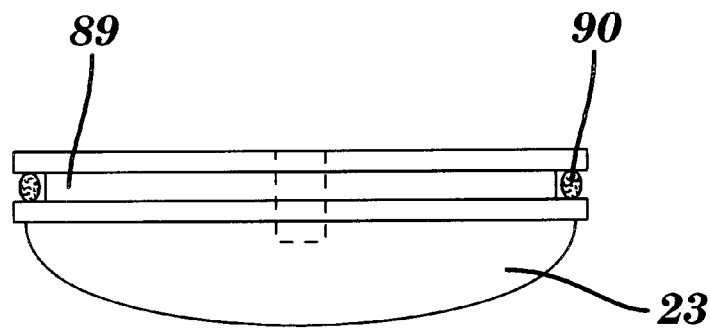
FIG. 16a shows a side view of a cooling head.
Figure 16B:
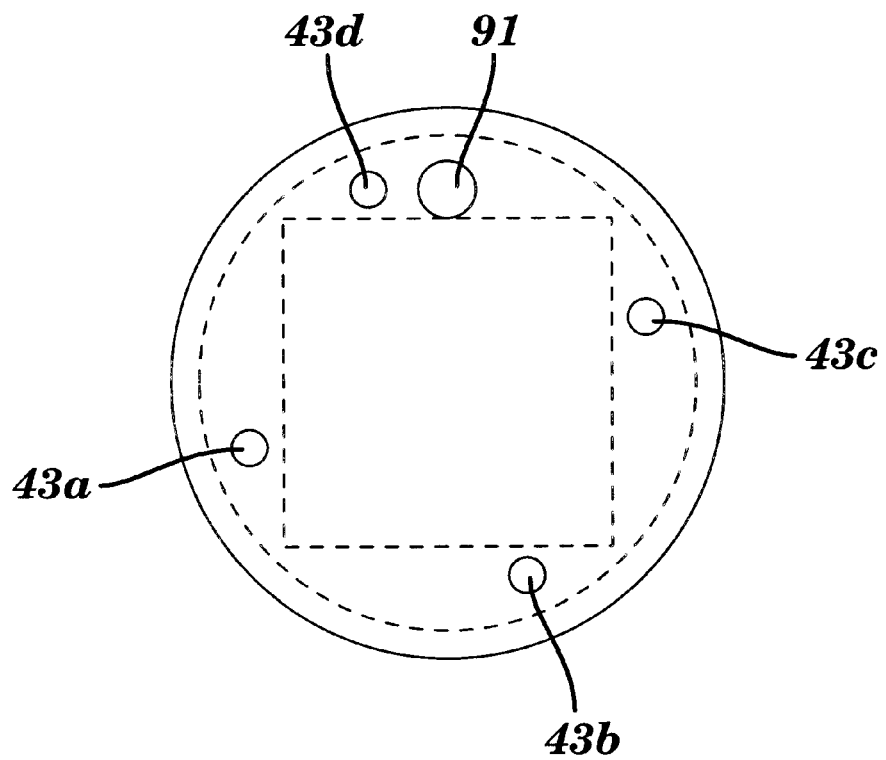
FIG. 16b shows a top view of a cooling head.

FIG. 16b shows a top view of the cooling head 23. Also the cooling head has a circular groove 89, into which an O-ring 90 for sealing may be fitted. The cooling head has four threaded screw holes 43a, 43b, 43c and 43d, having preferably a depth of 7 mm and being of type M3. These holes are preferably located at equal distances on the outline of a circle. Moreover, the cooling head has a hole 91 for the heat sensor. The holes 43a, 43b, 43c and 43d and the hole 91 leave enough space to mount on the cooling head a Peltier module, indicated by dashed lines forming a square on FIG. 16b. It is clear that the cooling head 23 has a larger surface than the surface of the lower plane of the cup 86 of the heat dissipation element. Therefore, it is advantageous to select for the heat dissipation element a metal having a higher heat conductivity (copper) than for the cooling head (aluminum), although the specific weight of copper is much higher than that of aluminum.

The cryoprobe is now mounted as follows. First, the temperature sensor is mounted in the hole 91 of the cooling head 23. By making use of thermal paste to fit the sensor in the hole, a good thermally conductive contact is obtained between the sensor and the cooling head. The thermal paste may comprise thermal conductive silicones, such as Dow Corning 340 "heat sink compound" or silver glue, such as 'AMICON ct 4042-32'. Then, the upper surface of the cooling head is provided with a layer of thermally conductive silicone. On that layer, the Peltier module is mounted, which then makes a good thermal contact with the cooling head. The upper side of the Peltier module is preferably also covered by a layer of heat conductive silicones. The conductors of the heat sensor are passed through the passage 88 in the heat dissipating element, and then the heat dissipating element is placed on the heat conductive silicones on top of the hot junction of the Peltier module. On each hole 46a, 46b, 46c and 46d of the heat dissipation element, a ring made of plastic is put, to thermally isolate steel screws form the heat dissipation element, and to galvanically isolate the water circuit from the cooling head. Then four screws made of stainless steel are passed through the rings and the holes 46a, 46b, 46c and 46d of the heat dissipation element, and screwed in the respective threaded screw holes 43a, 43b, 43c and 43d of the cooling head. The force on these screws is decisive for how strongly the Peltier module is pressed between the cooling head and the heat dissipation element. The screws made of stainless steel, may be replaced by plastic screws, preferably nylon. Such screws may cope with expansion and compression of the assembly due to temperature variation. This avoids excessive strain to the Peltier module. Due to the four screws, the thermally conductive glue has more importantly the function of heat conductive element than as glue. As such, the glue on the cold and hot junction of the Peltier module may be substituted by a thermally conductive paste or vice versa. In the grooves 85 and 89, the respective O-rings are mounted. The screwed assembly formed by the cooling head, the Peltier module and the heat dissipating element is now passed by pressure in the lower housing 21a, shown in FIG. 14b, from top to bottom. Preferably, PVC-glue is applied to the O-rings and to the heat dissipation element. Since the housing is preferably made of PVC-MZ, produced by Erics, the glue is compatible with the housing. Application of the glue improves sliding of the assembly in the lower housing. The assembly is shifted that far in the lower housing, such that the O-ring 92 of the cooling head strikes against the flange 83 of the housing. As such, the Peltier module will be saved from impact or shock, even if the cooling head bounces on a solid surface. Moreover, the O-rings provide a good thermal isolation, which is the key for good operation of the cryoprobe. Since the ceramic Peltier module is mounted floating by the O-rings, the module is much more shock resistant.

If the cryoprobe is used to warm up a surface, then the heat dissipation element is cooled by the Peltier module. By this action, the cooling fluid may freeze, if it were not provided with an anti-freeze medium, such as glycol. At the primary circuit, where the freon is expanded, the water may reach a temperature of −7° C. In such case, pure water cannot be used, since it freezes at 0° C. Where the freon is compressed in the compression/expansion system, the produced heat is dissipated by the ambient air.

In normal operation, the cooling fluid will circulate and will be cooled in the compressor. Since no use is made of a second Peltier module to cool the cooling fluid, and not use is made of an air/air system, but rather of a compression/expansion system, the temperature of the cooling fluid, and thus also the optimal operation of the Peltier module and the whole cryoprobe, is more independent from the ambient temperature. Even in an environment of 30° C., the system according to the current invention, still operates according to its specifications.

Figure 2:
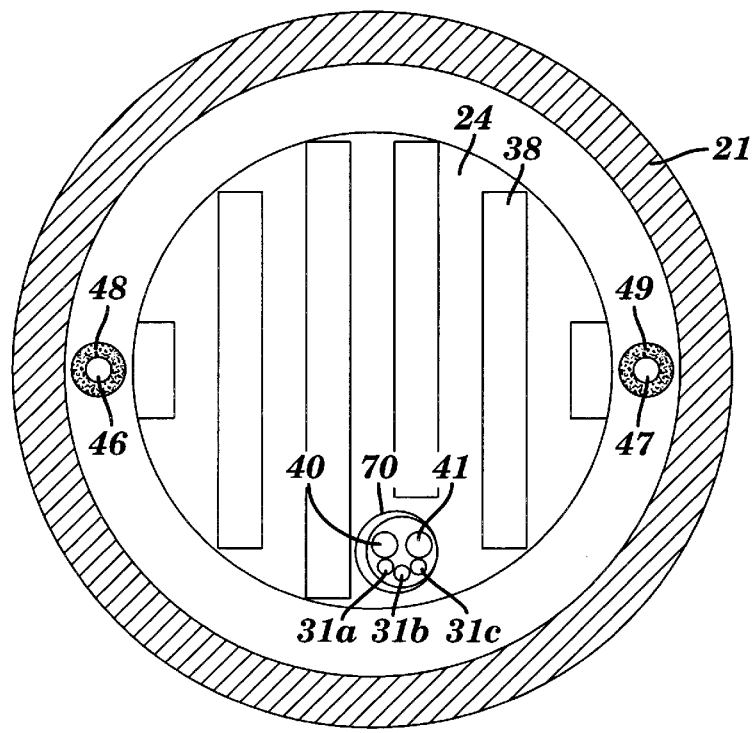
FIG. 2 is a top view of the cryoprobe according to a cross-section along the plane 1—1 in FIG. 1.

The most important operative part is the Peltier module 22 in FIGS. 1, 2. A Peltier module which is suitable for the cryoprobe according to this invention is of the type CP-1.4-71-045, manufactured by MELCOR.

A Peltier module is preferably composed of a number of thermally parallel, electronically serially coupled thermocouples. In the present case 71 thermocouples are used. A Peltier module is in principal a heat pump formed by a semi-conductor. At the "cold junction" or "cold side" of a Peltier module, the energy in the form of heat is absorbed by electrons (at their transition from the one semi-conductor to the other). These electrons are forced to move from a lower energy level to a higher energy level.

Figure 11:
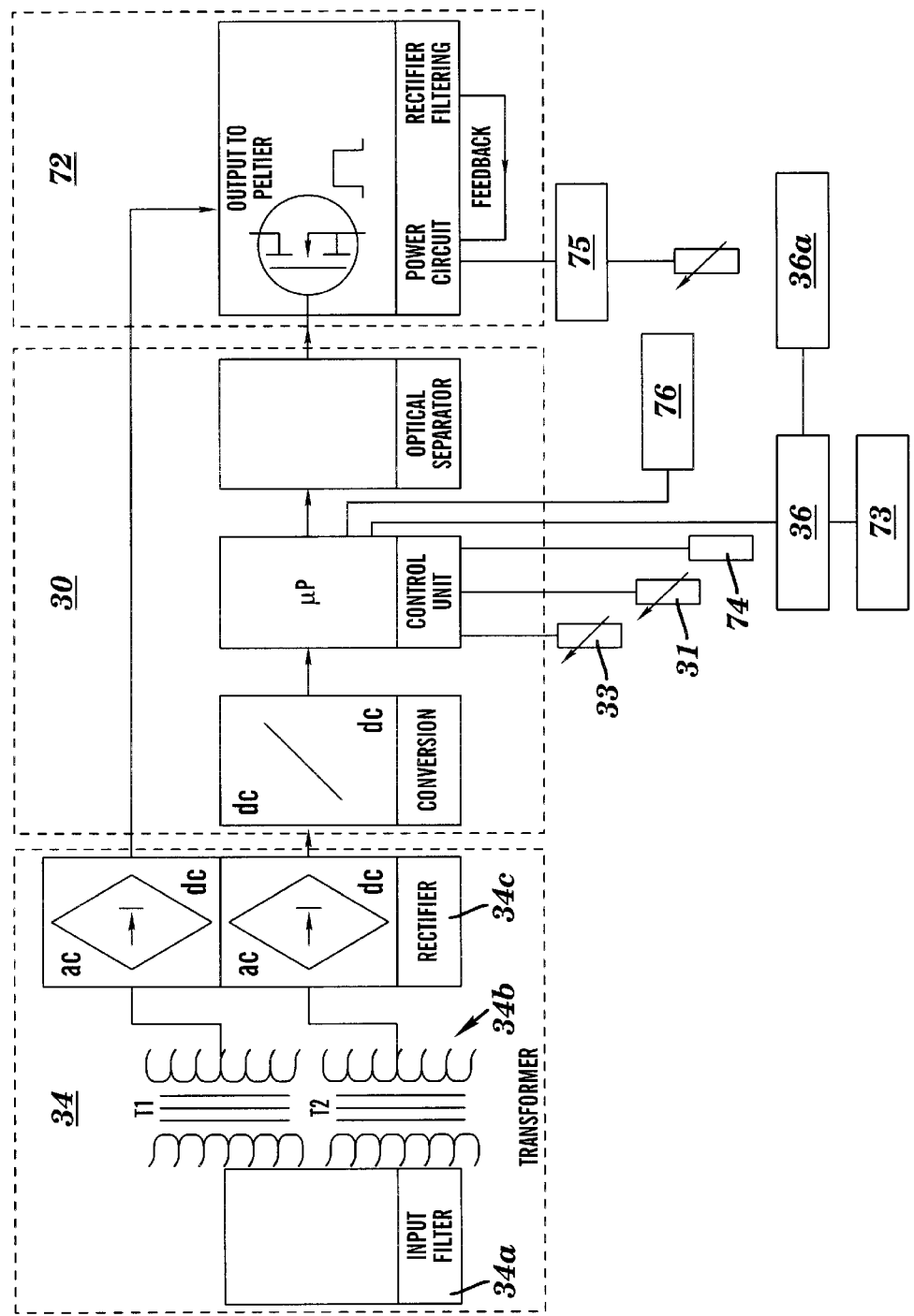
FIG. 11 shows a bloc diagram of the electronic control mechanism.

A voltage source, a current source or in general an electrical driving power supply 34 in FIG. 11, provides the energy to move the electrons through the semi-conductors. At the "hot junction" or the "hot side" the electrons move from a higher energy level to a lower one. There the energy is dissipated to the environment. This relates not only to the energy absorbed at the cold side, but also to additional energy, required to move the electrons through the semi-conductors of the Peltier module. The latter energy is, as said before, provided by the electrical source 34. FIG. 11 shows that 220 Volt is applied via the input filter 34a. This voltage is transformed and distributed in the control voltage T2 and the driving voltage T1, both at the required low voltage of 24 Volt. This alternating voltage is rectified in 34c.

Referring to FIG. 11 and FIG. 1, FIG. 1 shows two supply wires 40, 41 for the electricity, which are required to transmit the electrical energy from the electrical source 34 to the Peltier module 22, via the switched power supply 72. At the cold side of the Peltier module 22, a cooling head 23 is mounted. This cooling head has preferentially the form of a truncated cone, wherein the base surface must make a very good thermal contact with the cold side of the Peltier module and wherein the top surface serves to dissipate the heat from the surface to be treated. The top surface may also be shaped as a slightly spherical surface, such that the contact area with resilient surface to be treated can be increased by urging the cryoprobe more firmly.

Figure 3:
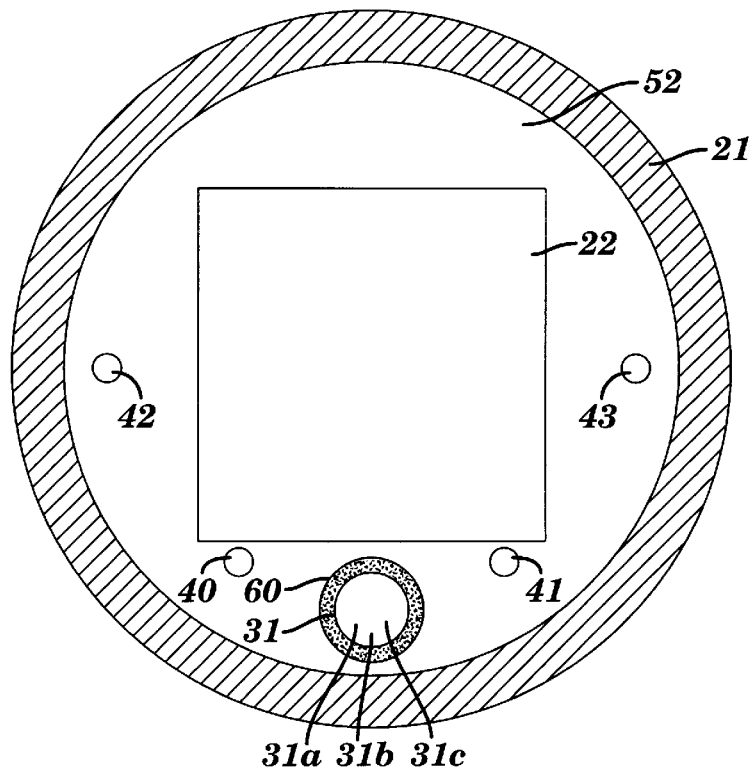
FIG. 3 is a top view of the cryoprobe according to a cross-section along the plane 2—2 in FIG. 1.

Referring to FIG. 1 and FIG. 3, a temperature sensor 31 is built in the cooling head 23, in the bore 60 of the cooling head. Its function is controlling the temperature of the cooling head. Therefore, the sensor transmits its data to the micro-controller 30b shows in FIG. 11, which in turn will compare the required temperature with that of the temperature sensor 31, in order to regulate the voltage applied to the Peltier module if necessary. It is important to determine a suitable algorithm for the temperature control. A proportional control is preferred, which may be incorporated in the Eprom of the control circuit 30b. Preferably the temperature sensor 31 is a thermocouple or a thermistor or a Pt100 or an NTC resistor or a PTC resistor, or a thermal sensitive diode producing 10 mV/°C., which provides between two conductors either a voltage, or a difference in resistivity as a function of the temperature. A temperature sensor 31 suitable for the current invention is for example an LM335 with connection wires 31a, 31b, 31c, shown in FIG. 2 and FIG. 3 and manufactured by National Semiconductor Corporation. In this case, a third conductor may be routed to the temperature sensor. The latter has the function to calibrate the temperature sensor if necessary.

The thermal contact between the temperature sensor 31 and the cooling head 23 must be carefully designed. Therefore, the temperature sensor may be mounted in a bore 60 in the cooling head 23, and embedded in glue or a thermal conductive paste e.g.: Dow Corning 340 "heat sink compound".

The amount of heat developed at the hot side of the Peltier element is roughly the same as:
the heat that must be dissipated at the cold side, added to:
the amount of electrical energy to be applied to the Peltier module, in order to operate as a heat pump.

It is not enough to cool the hot side of the Peltier module by the environmental air according to this invention, even not if it is guided in a forced manner via the hot side of the Peltier module. Even high-pressure air could be used in theory, but still gives not enough cooling. A good dissipation from the hot side may be achieved only by bringing a suitable dissipation element 24 in good thermal contact with the hot side of the Peltier module. The heat dissipation means 24 must be designed such that it is capable to dissipate the required amount of heat calories. Therefore the total surface and the construction of the cooling ribs and the thickness and length of the material are very important.

Moreover, the heat dissipation means according to our invention is preferably cooled almost permanently by a cooling fluid, preferably comprising 20% ethylglycol and 80% demineralised water. The cooling fluid transports the dissipated heat out of the cryoprobe.

This cooling fluid has preferably a good thermal conductivity. Moreover, the fluid is preferably forced by convection. The cooling fluid is preferably supplied by a supply passage 26 shown in FIG. 1, via a swivel 56 to a reservoir 25, and drained off by a drain passage 27 via a swivel 57.

The outer surface 21 of the internal reservoir 25 is preferably made of synthetic material. It is preferred that the synthetic material is good thermally insulative and on top of that it is important that the synthetic material is waterproof for 100% and has no absorptive power for the cooling fluid, such that no expansions of the material may occur.

In our invention we use PVC MZ material of the manufacturer: SIMONA. This material has a temperature range from −10° C. to 65° C., is very water repellent and has no nominal deformation in this temperature range. Moreover, the material can be perfectly glued. Preferably, the largest portion of the conic outer surface of the cooling head 23 is sealed from the environmental air by a thermally insulative synthetic material 59. Thereby, on the one hand the transmission of head from the environmental air towards the cooling head is minimal and on the other hand the occurrence of condensation on the cooling head is reduced to a minimum. As such, the cooling capacity of the Peltier module can be used optimally for the surface 64 to be treated. It is preferred to accommodate the synthetic material as good as possible to the outer surface of the cooling head, on two contacting lines: one at the base of the cooling head, where the Peltier module is mounted, and one near the top of the cooling head. Between those two contacting lines, the inner side of the synthetic material and the outer surface of the cooling head, it is preferred to provide a thin air gap. The static air provides there an extra thermal isolation, and through the narrow contacting lines no environmental air can flow inside. As such, as described before, the damp environmental air cannot condensate on the outer surface of the cooling head. Preferably the outer surface 54 of the internal reservoir 25 of the cryoprobe and the cover of the outer surface 59 of the cooling head 23 are formed by a one-piece synthetic housing 21. This synthetic housing preferably has internally a circular cross-section, which considerably alleviates assembly of the internal parts of the cryoprobe, especially with respect to the sealing parts. Moreover the external surface of the housing may be predominantly circular, which increases considerably the ease to handle. However, that external surface may have also an irregular shape, which improves the design and ease to handle. It is also possible to provide recesses, grooves and the like in the outer surface of the housing 21 to ameloriate the ease to handle. An important feature of the cryoprobe according to the current invention is that an optimal heat transport is achieved throughout the whole system, except
from the heat dissipation element 24
to the cooling head 23.

Moreover a fast temperature change of the cooling head must be possible, to allow for specific hot and cold treatments. As known, the direction of cooling or heating of a Peltier element and of a module is determined by the determination of the polarity of the electric DC voltage. This change may be controlled by an operator panel 73, shown in FIG. 11. Therefore, several measures may be taken.

First of all, it is very advantageous to make the cooling head 23 of a solid material having a very high thermal conductivity and a low thermal inertia or heat capacity. By the high thermal conductivity, it is achieved that the temperature of the cooling head has an equal value on almost all locations. This is advantageous to cool or heat continuously the surface to be treated. Moreover, the temperature sensor 31, wherever it is located in the cooling head, will always give faithfully the exact temperature, which is almost equal within the complete cooling head. The low heat capacity provides a fast reaction of the cryoprobe upon the desired temperature changes. If the cooling head must be heated suddenly by the Peltier module to increase the temperature by 5° C., then the Peltier module must supply an amount of heat which is proportional to the temperature difference (5° C.), the mass of the cooling head and the heat coefficient. Because the Peltier module is capable only to supply or absorb a maximum heat flow or amount of heat per unit of time, a low heat coefficient for the material of the cooling head is advantageous to reduce the total reaction time.

A suitable solid material for the cooling head 23 is a metal, preferably aluminum. An alloy that mainly consists of aluminum is also very suitable for the cooling head of the cryoprobe according to the current invention. On the one hand this complies with the above mentioned requirements with respect to the heat coefficient and on the other hand this material has a low weight and is easily machined in lathes and milling machines, which is an important prerequisite for production. Other alloys of metals with other materials may have also the desired advantageous effects. It is also preferred to anodise all aluminum parts, with a thickness of preferably 25 μm, to protect it against oxidation by the cooling fluid and the environmental air at the cooling head 23. To ensure an optimal heat transport
via the contact surface 52 between the cold junction of the Peltier module and the cooling head at one side; and, via the contact surface 53 between the hot junction of the Peltier module and the heat dissipation element at the other side, it is advantageous to prevent heat barriers. A good heat transport via these contact surfaces may be achieved in the first place by urging the elements tightly against each other.

According to a first embodiment we provide the base of the cooling head 23 with two holes 42, 43, shown in FIG. 1 and FIG. 3, both holes provided with inner thread. In the heat dissipation element 24, there are provided two bores 46, 47. Each of these bores are provided at the upper side with a sealing ring 48, 49, shown in FIG. 2. These rings prevent on the one side that the cooling fluid of the reservoir would penetrate in the cylindrical bores 46, 47. On the other side, these serve also as insulation between the cold side and the hot side. When assembling the cryoprobe, in each bore 46, 47 and through the sealing rings 48, 49, a screw 44, 45 is passed, and screwed in the corresponding threaded hole 42, 43 in the cooling head 23. Both screws are screwed tightly, preferably up to a pulling force of about 1 Kg/cm.

Thereby the cooling head 23 is urged tightly against the cold junction of the Peltier module 22 and the heat dissipation element 24 is urged tightly against the heat junction of the Peltier module 22. It is possible to replace one screw by a clip or brace as described in patent application WO 87/07361. Such a clip or brace connects the cooling head with the heat dissipation element, using the suitable grooves in the housing 21. As such, only one screw must be mounted. As said before, it must be avoided that an unwanted heat flow is created between the cooling head 23 and the heat dissipation element 24. The screws 44, 45 may therefore cause a problem. Therefore, these screws are preferably made of a thermally insulating material, e.g. nylon or glass fibre. In another preferred embodiment, stainless steel is used, because it has a low heat conductivity and therefore is suitable to manufacture these screws.

To further improve the heat transport via the contact surfaces 52, 53, it is preferred to maximise the microscopic contact surface. This may be done by making one of the contact surfaces very smooth, and preferably by grinding and polishing, preferably with a tolerance of ten micrometer. This may be done to the basis of the cooling head 23, that is brought into contact with the cold junction of the Peltier module. This may also be done with the contact surface of the heat dissipation element 24, which is brought into contact with the hot junction of the Peltier module.

When polishing finer than the above tolerances, the extra costs are almost not balanced by the realised improvement of the heat transport. The cold side and the hot side of the Peltier module are preferably polished at manufacture up to a high precision of 2 micrometer.

To further improve the thermal transfer of the above described contact surfaces, it is advantageous to provide a thermally conductive paste between both. An example of a suitable conductive paste is "Head sink compound 340" manufactured by: Dow Corning.

Another way to avoid the use of paste is the use of thermally isolating foils or patches between the aforementioned contact surfaces. For example, silver patch or copper patch may be used. These patches are fairly good thermally conductive and have a good mechanical strain capacity, because they are not hard and well deformable. A known manufacturer of these is for example: the company "Kunze Folien" or for example "Sarcon" from the group "Fujipoly". These manufacturers offer a whole gamut of synthetic-like rubbers and of carbon foils which are good thermally conductive. A last embodiment that offers the best thermal mechanical properties, is gluing, which allows to dispense with the screws 44, 45 shown in FIG. 1. Glue may avoid extra polishing and a thermal conductive paste. The function of the latter three provisions may be achieved by making use of a thermally conductive glue. On the market, such a basic glue is offered, having high electrical conductivity, for application in microelectronics. The company "Grace NV" offers such glue on the market under the trade name: 'AMICON ct 4042-32'. This is a registered trade name of "W.R Grace and Co". This glue is a two-component epoxy-glue, which comprises a lot of silver to improve the electrical conductivity. This glue has a high tensile strength and a high heat durability.

Tests with the cryoprobe according to the current invention have shown that this type of glue provides also a high thermal conductivity, which is of course a big advantage for the apparatus.

Our lab tests show that a problem may show up when gluing. When the glue dries or hardens, its structure shrimps, because the solvents evaporate, whether these harden chemically or by means of extra heating. This gives in many cases microscopic or tiny irregular structures, where glue is not homogeneously distributed. Even worse, despite a glue thickness of only 70 micrometer, conspicuous air bubbles may be created.

This phenomenon considerably reduces the total conductivity coefficient on the aforementioned contact surfaces. To solve this problem the glued parts may be dried under vacuum. However, while this is practically difficult to achieve in production, the following modification was made:

- To the composition of the glue, preferably 1% "spacer" is added; this "spacer" is a particle developed by us, having a thickness of preferably 50 micrometer and preferably made of a silicon alloy. To maximise the efficiency, this particle may be covered by a metallic layer, preferably silver.
- When gluing, preferably a constant thickness layer is left, having the size of the thickness of the particles used. According to our invention it is advantageous to apply 2.5 gramme of glue by means of dispensing the glue in 5 dots of 0.5 gramme each on the surface of 9 cm$^2$.
- When the parts are assembled, a small mechanical force of preferably 300 g is applied on top of the part to be glued.
- For the hardening process, the thickness of the glue layer is somewhat larger and after evaporation of the solvents, a continuous thickness profile all over the glued surface is obtained, without any perceptible air bubbles.

The small weight of 300 g is suitable for a surface of the portion to be glued of the cooling head of 9 cm$^2$, which is applied in the current invention. The useful glue surface equals of course to the maximum dimension of the Peltier module. This gives for the current invention a very suitable connection technique between the cold junction and the cooling head; and between the hot junction and the heat dissipation element;

both mechanically and thermodynamically. The cryoprobe may be mounted preferably according to the following method.

1) the base 52 of the cooling head and or the cold junction of the Peltier module is provided with a thermally insulating glue.
2) the base 52 and the cold junction are brought on top of each other.
3) base 53 of the heat dissipation element and/or hot junction of the Peltier module is also provided with the thermally conductive glue.

4) base 53 and the cold junction are brought on top of each other.
5) the whole assembly is put into a model or holder such that horizontal movements are disabled. On top of the assembly, a weight of preferably 300 g is put.
6) the electronics are connected as thermostatic circuit to control the temperature and an alternating voltage is applied to the Peltier module. Thereby the Peltier module will, differently from its normal use, heat completely at both sides up to a temperature of preferably 110° C.
7) as soon as the temperature is above 110° C., the alternating voltage is switched off, under 110° C. switched on again.
8) Step 7 is repeated preferably 30 minutes until the glue is completely hardened.

The hardening of the glue may also be achieved by externally heating the complete system described before in for example an oven of which the temperature may be fairly good controlled. It is not necessary that the thermally conductive glue only contains silver. Other good thermally conductive filling materials may be advantageous e.g. an alloy of manganese.

According to yet another embodiment, the base of the cooling head 52 is soldered on the cold junction of the Peltier module. It is also advantageous to solder the base of the heat dissipating element 53 on the hot junction of the Peltier module. Also this process is preferably done in an over. However, the temperature must not raise above the data of the manufacturer, to ensure the lifetime of the Peltier module. To optimise the heat transport between the heat dissipation element 24 and the cooling fluid, it is advantageous to provide the heat dissipation element with preferably one cooling rib 38. Thereby the contact surface between the cooling fluid and the heat dissipation element increases. This contact surface may be further increased by providing a plurality of cooling ribs. It is also possible to operate without a cooling rib.

The heat dissipation element must properly separate the cooling fluid from the chamber where the Peltier module is located. This may be achieved by a perfect mechanical fitting between the heat dissipation element 24 and the housing 21 by means for pressure. The same applies for the cooling head 23 and the housing 21, to achieve a perfect mechanical fitting. A preferred way to achieve this is to make the heat dissipation element disk-like or cylindrical, with a circular recess for an O-ring 37, shown in FIG. 1. The recess is made in the outer surface of the cylinder. The O-ring urges with its outer side against the cylindrical inner side of the housing 21, and with its inner side against the recess in the outer surface of the heat dissipation element 24. Thereby an optimal sealing for the cooling fluid is achieved. It is preferred to make the O-ring from Teflon material. Other materials may also be envisaged, as long as they are resistant against the cooling fluid and rapidly changing temperatures. The reservoir 26 is preferably sealed on top by a disk-like lid 50, which rests on a flange 55 in the housing 21. During assembly, this lid is glued on the flange. As described before, the electrical conduits or wires 40, 41 serve to provide the Peltier module with electrical energy. These wires could be guided laterally to the cryoprobe. This has however practical complications for the ease of handling the apparatus. It is advantageous that these wires enter the apparatus via the top side, together with the supply and drain of fluid. The electrical wires 40, 41, 31*a*, 31*b,* 31*c,* shown in FIGS. 1, 2 and 3, must reach the Peltier module via the cooling fluid, thereby avoiding that the cooling fluid reaches the Peltier module. Therefore it is preferred to provide a sealing tube 39, shown in FIG. 1. This tube 39 starts in the air chamber 51 and is there also sealed by the O-ring 55 in the lid 50. The tube 39 continues up to a circular bore in the heat dissipation element. During assembly, the sealing tube 39, at the bottom of the heat dissipation element, is preferably glued. Gluing may be performed by means of two-component epoxy glue such as a glue having trade mark "CIBA-GEIGY" with the trade name "Araldite". This sealing tube 39 may be equally used to guide the wires or conductors 31*a,* 31*b,* 31*c,* shown in FIG. 2 and FIG. 3 of the temperature sensor 31 from the air chamber 51 to the cooling head 23.

Figure 9:
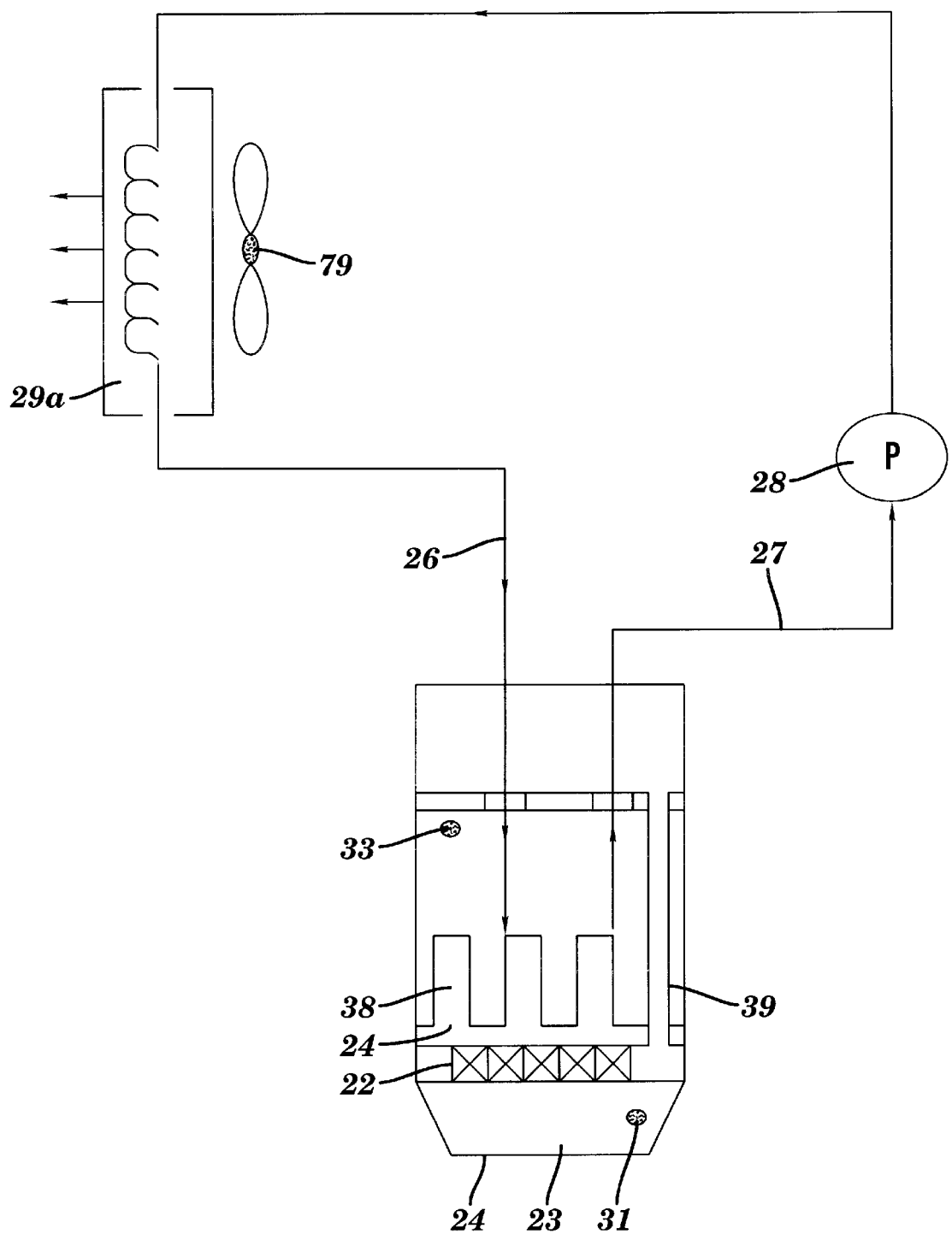
FIG. 9 shows a schematic presentation of heat-exchanger air/fluid cooling.

A suitable cooling fluid having a favourable price is water. Pure and free cooling water may be taken mostly directly from the waterworks. The supply conduit-pipe 26 is thus connected to a tap, whereas the drain conduit-pipe 27 may be connected to a drain of a domestic installation. The cryoprobe in operation requires, dependent upon the temperature of the water, a rate of flow of the water of 1 liter per minute. In industrialised countries, where the tap water has a sufficiently low average temperature of 10° C., this may be a suitable solution, provided that in series with the filter of the waterworks, a small demineralisation unit for water is installed in addition. It would be advantageous to provide a closure valve in the supply conduit-pipe, which allows for water to be supplied subject to electrical driving by the control electronics, and which closes the supply as soon as on the one hand a specific program of the cryoprobe ends, to prevent spillage of water, and which on the other hand closes the water circuit when a fault in the system occurs, for example a leak in the supply pipes. Where the availability of tap water for cooling is problematic, the cooling fluid may circulate in a closed loop, as shown in FIG. 9, having a circulation pump 28. It is also advantageous to add glycol to the water in the closed loop, preferably about 20%. This is to prevent that by heating the cooling head 23, the heat dissipation unit 24 would start cooling under zero degrees Celsius and in the water reservoir 26, the pure water would freeze.

The circuit must then also comprise a heat-exchanger 29, that dissipates the heat of the cooling fluid to the environment, as shown in FIG. 9. The heat-exchanger is preferably a (cooling) fluid/air heat-exchanger, with forced air cooling. Of course the system is then still dependent on the environmental temperature, which may considerably influence the efficiency of the probe. This is because the lower the temperature of the hot side, the more the system can cool at the cold side. This will be clarified below.

THERMOELECTRICAL PHENOMENA

Introduction

Figure 4:
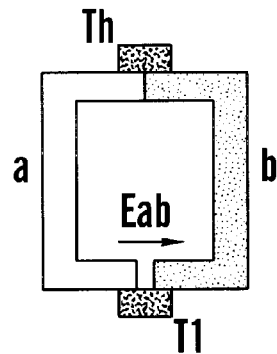
FIG. 4 shows the Seebeck-effect.

Thermoelectrical effects are associated to combined heat- and electricity-flows. The two most commonly known effects are the Seebeck-effect and the Peltier effect Seebeck effect FIG. 4 Seebeck effect.

When two different wires a and b for a circuit, and the junctions, $T_h$ and $T_l$ have a different temperature between a and b, then a voltage difference may be noticed. This voltage $E_{ab}$ is the Seebeck-voltage and seems to be proportional to the temperature difference:

$$E_{ab} = S_{ab} \Delta T = \Delta T = Th - Tl$$

with $S_{ab}$ the relative Seebeck-coefficient between the materials a and b.

Peltier effect

Figure 5:
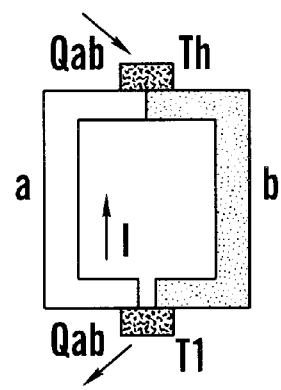
FIG. 5 shows the Peltier-effect.

FIG. 5 Peltier effect.

When a current is sent through a circuit consisting of two different materials, a and b, then at one junction $T_h$ heat will be absorbed and at the other junction $T_l$ heat will be released. The amount of heat $Q_{ab}$ is proportional to the current I, $$Q_{ab}=\Pi_{ab}I,$$

with $\Pi_{ab}$ the relative Peltier coefficient between the two materials a and b.

Lord Kelvin discovered on the basis of thermo-dynamical principles that the Seebeck- and the Peltier-coefficient are related to each other, $$\Pi_{ab}=S_{ab}T.$$

Intermezzo: physical interpretation

Free electrons move in a metal at a determined energy level, dependent upon the metal. When two different metals come into contact with each other, the electrons in the metal at the highest energy level will flow to the metal with electrons at a lower level. The effect is that the metal with the lowest energy level gets more electrons, and is charged negatively The voltage, that is built up in that way, will prevent even more electrons to flow: an equilibrium is created. This voltage is specific for two materials.

This voltage can not be measured, since each attempt for a measurement requires new junctions (i.e. with the wires to the volt-meter), resulting in voltages eliminating each other.

The voltage difference which is created is however temperature dependent. When two junctions are made, which are at a different temperature level, a nett voltage difference will result, which may be measured. This voltage is the Seebeck-voltage. It is proportional to the temperature difference and dependent on the type of materials. When a a current is forced through a circuit consisting of two different metals, the electrons must go "up" at the one junction (from a lower to a higher energy level). To get up, they will absorb energy from the environment, i.e. cooling (such as e.g. also evaporating acetone absorbs heat from the environment). On the other junction the electrons will fall "down" and release energy, i.e. release heat. The amount of heat that is dissipated from the cold side is dependent upon the number of electrons that flow per unit of time, this is the current.

This is the Peltier-effect

THERMOELECTRICAL COOLING

Introduction

Figure 6:
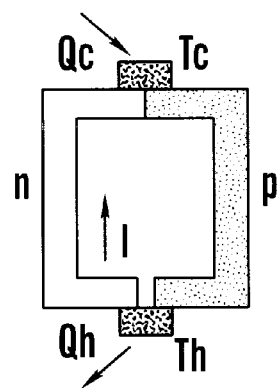
FIG. 6 shows a presentation of a theoretical cooling apparatus.

FIG. 6 Cooling apparatus.

We discuss the cooling capacity of a simple Peltier-circuit, consisting of an n- and a p-leg. Three effects must be studied therefor: the Peltier-effect at the junctions, the Joule-heat, produced by the current that flows through the circuit and the heat-conduction through the legs.

Maximal cooling

The energy-balance of a Peltier-cooler may be written down if we take into account three heat-flows:
- the Peltier-effect at the junctions, with previously described formulae this becomes S T I, with S the Seebeck-coefficient, T the temperature of the junction and I the current through the element.
- the Joule-heat amounts to $RI^2$, with R the electrical resistance. A detailed analysis (with differential equations) teaches us that exactly half of the Joule-heat flows to the hot junction and exactly half to the cold junction.
- the thermal conductivity $K\Delta T$, with K the thermal conductivity and $\Delta T$ the temperature difference. The two junctions are at a different temperature, therefore heat flows form the hot to the cold side.

The energy balance (i.e. the heat $Q_c$ which is absorbed at the cold side and the heat $Q_h$ which is released at the hot side) is then $$Q_c=ST_cI-K\Delta T-\tfrac{1}{2}RI^2,$$

$$Q_h=ST_hI=K\Delta T-\tfrac{1}{2}RI^2, \quad (1)$$

The purpose is to cool maximally, i.e. to maximise $Q_c$. Therefore we take the first derivative:

$$\frac{dQ_c}{dI}=ST_c-RI=0.$$

This equation holds if $$R=\frac{ST_c}{I}. \quad (2)$$

R is determined by parameters of the metal and the geometry.

$$R=\rho\frac{1}{A}.$$

The resistivity r is determined by the material with which we are working. Equation (2) thus imposes a restriction to the geometry (a ratio between the length l and the cross-section A) once the operational current is determined. Because the geometry is now determined, also K is fixed, $$K=\kappa\frac{A}{l}.$$

with k the thermal conductivity.

If, in equation (1), we substitute R by equation (2), we get:

$$Qc=\tfrac{1}{2}ST_cI=K\Delta T$$

In this equation we can see that the maximal cooling power is determined by the Seebeck-coefficient S (material parameter), the temperature of the cold junction $T_c$ (design-parameter), the current I (controllable, but bonded by the maximal current density), the thermal conductivity K (is fixed by optimising the geometry) and $\Delta T$ (determined by the cooling power at the hot junction).

The cooling power may thus be maximised by minimizing the temperature difference $\Delta T$, i.e. by cooling the hot junction as much as possible.

The voltage that we must apply on the element consists of two portions: the voltage drop across the resistor $\Delta V=RI$ and the Seebeck-voltage caused by the temperature difference between the two junctions $\Delta V=S\Delta T$. The total supplied power is then $$P_{in}=VI=(S\Delta T+RI)I=S\Delta TI+RI^2.$$

Also here one can see that the supplied power may be minimised by decreasing $\Delta T$.

Some parameters

For the Peltier-element in this invention ($U_{max}$=8V; $I_{max}$=8.5 A; $Q_{max}$=38.5 Watt at $T_h$=25° C. and $\Delta T_{max}$=67° C.), some curves were computed.

Figure 7:
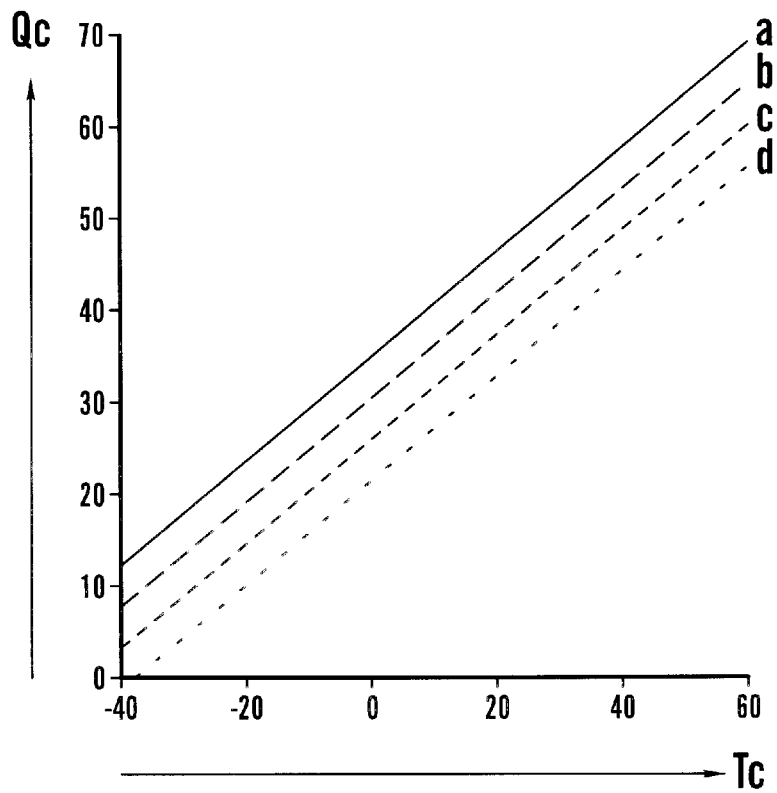
FIG. 7 shows the maximal cooling power $Q_c$ as a function of the temperature $T_c$ at the cold junction of the Peltier module.

FIG. 7 The maximum cooling power as a function of the temperature at the cold junction, computed for some temperatures at the hot junction (the linear curves a=0° C., b=15° C., c=20° C., d=30° C.)

Figure 8:
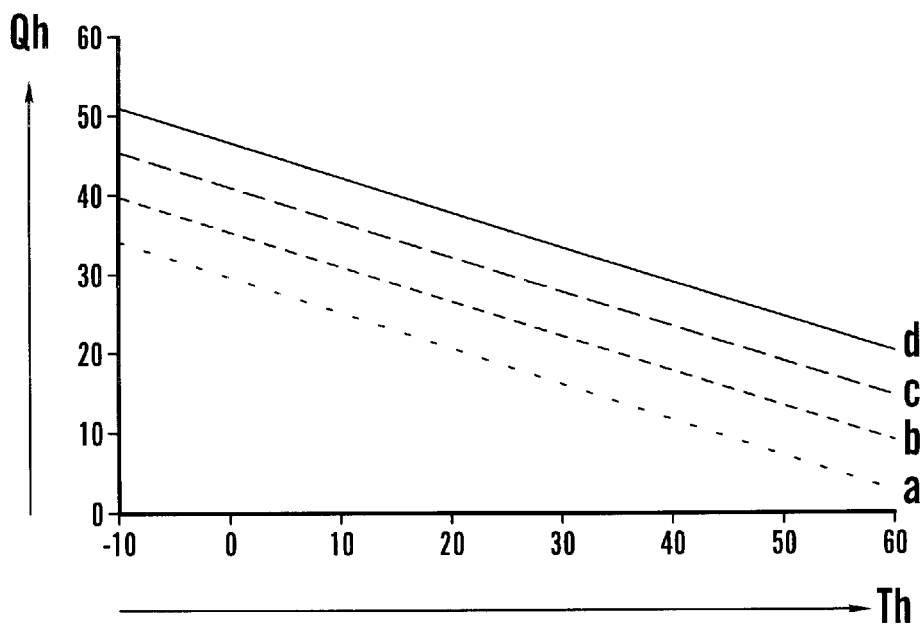
FIG. 8 shows the maximal cooling power $Q_h$ as a function of the temperature $T_h$ at the hot junction of the Peltier module.

FIG. 8 The maximum cooling power as a function of the temperature at the hot junction, computed for some temperatures at the cold junction (the linear curves a=−10° C., b=0° C., c=10° C., d=20° C.)

From the above deducted formulae and graphics it is clearly proven that: the maximum cooling power to be delivered can be achieved only if the hot side of the Peltier module is kept as cold as possible or said differently, approaches as close as possible the required temperature, if we want to keep this temperature constant at any price. It may thus be said that it is an art to dissipate the heat from a Peltier module in the correct manner, to make use of the highest efficiency. This feature is maximally exploited according to the current invention.

If the environmental temperature is too high, then it is also advantageous to work with a heat-exchanger, which is provided with one or more Peltier elements. The heat of that element may be released preferably via a large cooling rib, by using cooled ventilation.

Figure 10:
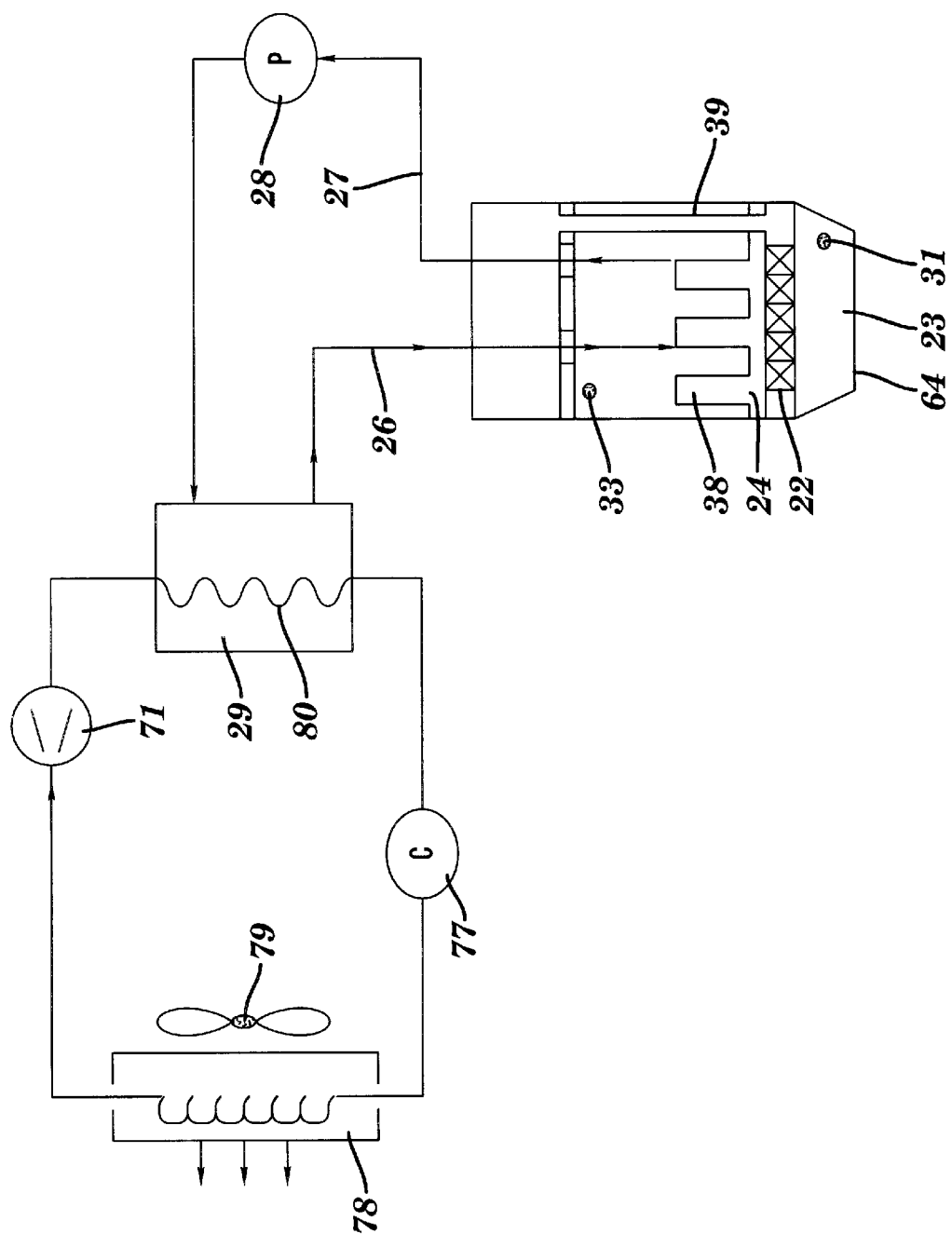
FIG. 10 shows a schematic presentation of heat-exchanger with a compressor cooling device.

The best way to be almost not dependent from the temperature of the environmental air, is to provide the heat-exchanger 29, shown in FIG. 10 with a gas conduit with an evaporator 80. This evaporator will absorb its heat according to the compression/expansion principle. Here follows a brief explanation of this principle: before the compressor, 71 just saturated vapour is present, which is compressed to obtain super-heated vapour. This vapour goes to a condenser 78, which converts the super-heated vapour to just saturated fluid. This fluid at high pressure flows then through a capillary tube 76, where it goes from high to low pressure. The length of this capillary tube determines the pressure drop and therefore the evaporation temperature of the gaseous mix. Thereafter, this gaseous mix flows into the heat-exchanger 29, whereby this gas tube 80 absorbs its heat from the environment. As such, the cooling fluid will cool down to the desired temperature. This system is applied traditionally in refrigerators for domestic use. In the current invention mostly a compressor of the brand "Danfos" and the type PL50fxno was used. This compressor is capable to pump away enough heat, to get in this way the cooling water at the required temperature. The compressing and expanding fluid may be for example "freon R 134 a". FIG. 10 shows a block diagram thermodynamic plan.

FIG. 11, reference numerals 34, 30 and 72 show the electronic control of the Peltier module. This control is preferably a source 34, 30, 72, for which the current and the voltage are controllable. The current control 75 is very important because a typical feature for a Peltier element is: its internal resistance decreases according to the operation time. Thus, if no current control is applied, after some time the resistance would drop and the current would increase. The current would raise above the maximum programmed current, which the manufacturer specifies. The consequence would be that at the one hand the cooling will decrease enormously and on the other hand the Peltier elements will be damaged very soon up to a final end. Therefore, the electronic control and the switched power supply 30, 72 controls permanently the maximum current and voltage. When the maximum current is exceeded, the electronics will power down the whole system, also precautionary.

If the temperature of the cooling head is varied according to a desired pattern in time, and also specific boundaries must be imposed to the temperature or temperature variations, it is advantageous that the electronic control 30 gets its power from a DC/DC conversion 30 to clean all noise that may enter via the means. The information with respect to the temperature profile may be obtained from an internal program loaded in Eprom 30b; and, on the other side information from its external temperature sensors 33, 31.

The temperature sensor 31 (FIG. 3 and FIG. 11) in the cooling head 23 preferably gives the necessary information to the electronics to control the temperature of the cooling head. This is however not possible in a usual thermostatic circuit with an on/off control. The high driving currents would damage the Peltier because of the big thermal shock that is would need to cope with, due to each time the maximum current on and off.

A precise control up to 1° C. would be difficult. A proportional control is advantageous and is a feasible solution to be programmed on for example an IBM computer via the input 76. A proportional controller controls continuously the variable to be manipulated, and thus the ratio between the set and read value of the temperature sensor 31a, b, c. In this way, the desired process temperature (set Setpoint) is kept constant.

At a large temperature difference, the voltage will raise with large jumps, at a small measured difference with small steps until the desired temperature is achieved. This regulating process is located in the micro-processor portion, 30b. The signal is first of all optically separated in the optical separator 30c because of safety reasons. Then the signal is set to the switched power supply 72 to supply a perfect output voltage to the Peltier module. Thus, preferably the electronic control 30 is provided with a control panel 73 to set the desired temperature of the cooling head. The desired temperature may be fixed for example between minimum −10° C. and maximum +45° C. The desired temperature may even be programmed as a function of the time. For ease of use, it is advantageous to provide the electronic control with a display 36a, on which the temperature process may be followed. It is also advantageous but not necessary to provide a second display 36, to be able to read out via menu driven software the settings. The electronic control 30 may for example be realised by a micro-controller of the type D87C51FA of the brand Intel. An I/O-port of the microcontroller may control a controllable current source of the type NFS-110-7912 of the brand "RS" to transport the desired electrical energy to the Peltier module in the cryoprobe. Therefore the voltage and the current of the power supply must be good controllable. The electronics have also the possibility to take over all the functions of the microcontroller towards a standard IBM compatible PC 76. The output value is preferably determined by the electronic control 30 as a function of the measured temperature of the cooling head and the desired temperature of the cooling head, set by the user. It is also important for the efficiency of the Peltier module that a good DC voltage is offered, on which few noise is present, preferably less than 5%. This may be achieved by the switched power supply 72. The voltage which is offered to the Peltier module is dependent on the type of the module and on the manufacturer. Because the system according to the current invention is a medical application, it is preferred not to go higher than plus 24 volt and all electrical standards relating to leakage current, and fire safe components must be taken into account. If the cooling head must cool, the sense of polarisation of the voltage of the Peltier module is that which is determined by the manufacturer and connected as such. If the cooling head 23 must produce heat, then the current supply is reversed, such that the cold junction of the Peltier module produces heat, and the hot junction absorbs heat from the heat dissipation element 24 and the cooling fluid. To improve the safety of the cryoprobe, the reservoir for the cooling fluid 25 is preferably provided with a temperature sensor 33. With that sensor, the temperature of the cooling fluid is controlled and the voltage of the power supply on the Peltier module is switched off if this temperature raises too high. This may happen if a breakdown of the supply of the cooling fluid would occur, or if a water pump breaks down or by a break down when use is made of a compression cooling device, as shown in FIG. 10. By making use of a compression cooling device, it is preferred to mount into its housing a small tilt contact 74, FIG. 11. The tilt contact may have the brand RS, with type "337-289". This contact must continuously control whether the tilt angle of the compressor dues not exceed the value specified by the manufacturer. Otherwise, fluid could in the compressor and destroy it definitively. It is preferred to connect the tilt sensor with an electronic time mechanism, which always reports to the micro-controller when such above mentioned problem could occur. This has as a consequence that, if a tilt report would enter, immediately an operation stop happens and a waiting time of preferably 4 hours starts for protection, before the machine may start again. This process may also be controlled when the device is without power, by means of an internal battery which provides power to a flip-flop, which on its turn memorises the status of the tilt sensor.

Figure 12:
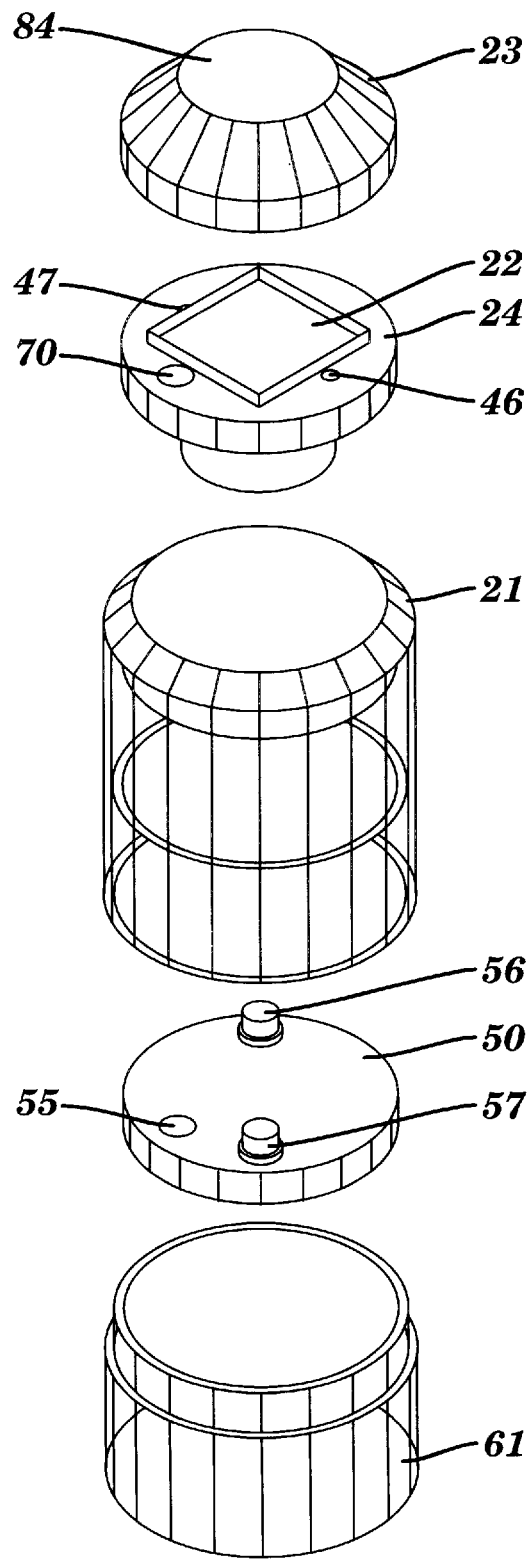
FIG. 12 shows in an exploded view the most important parts in a three-dimensional model of the cryoprobe according to the current invention.
Figure 13:
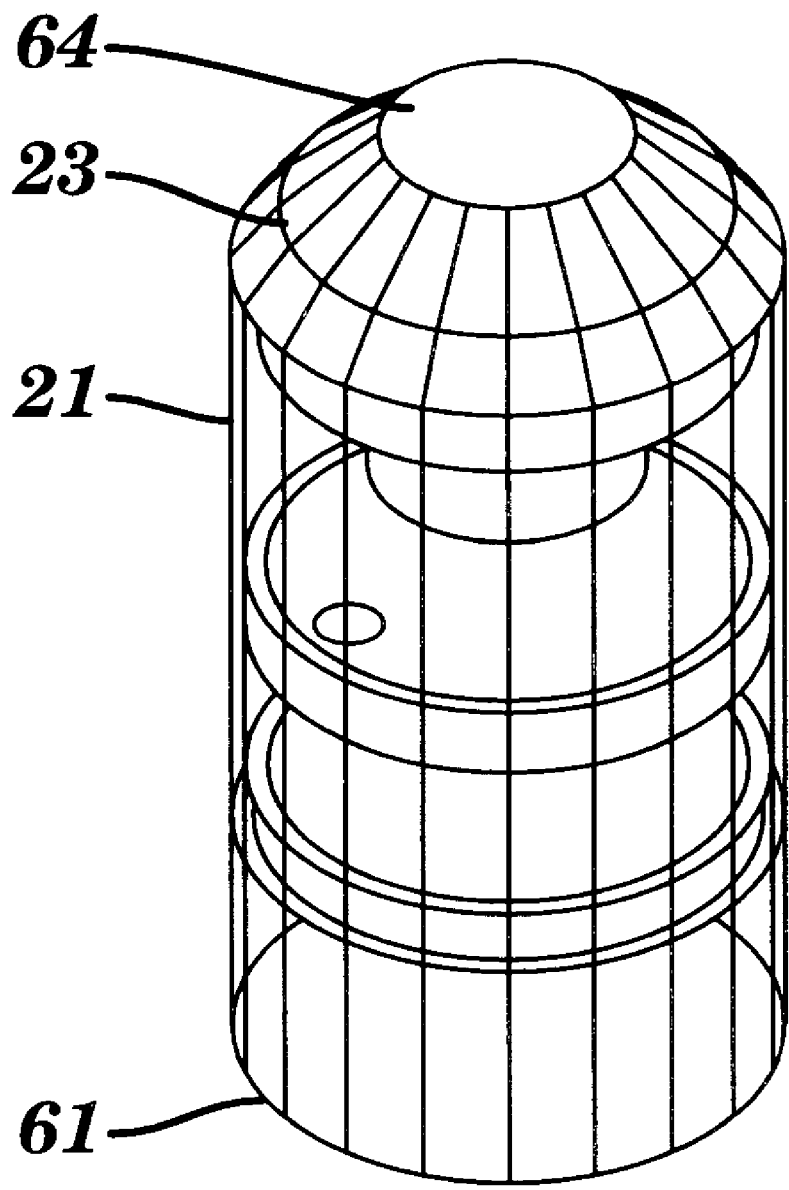
FIG. 13 shows a three-dimensional view of the assembled cryoprobe according to the current invention.

FIG. 12 shows an exploded model of the cryoprobe according to a preferred embodiment of the invention. FIG. 13 shows the corresponding composite three-dimensional model. All parts of FIG. 12 are provided with the numbers corresponding to FIG. 1. Their function and interrelation corresponds as described hereinbefore in conjunction with FIG. 1. It is clear for the man skilled in the art that modifications in each improved form and details may be provided without departing from the scope of the invention, as defined in the following claims.

What is claimed is:

1. A cryoprobe comprising:

a Peltier module with a cold side and a hot side;

a system for supplying electrical energy to said Peltier module;

a cooling head thermally coupled to said cold side of the Peltier module, the cooling head having a convex curved surface;

a heat dissipation element thermally coupled to said hot side of the Peltier module; and a reservoir for a thermally conductive liquid thermally coupled to said heat dissipation element.

2. The cryoprobe according to claim 1, comprising a compression/expansion system for cooling said liquid.

3. The cryoprobe according to claim 1, comprising means for joining said Peltier module, said cooling head and said heat dissipation element in a floating relation.

4. The cryoprobe according to claim 1, wherein the cooling head is made of metal mainly consisting of aluminum and the heat dissipation element is made of metal mainly consisting of copper.

5. The cryoprobe according to claim 1, wherein at least one contact surface between the cooling head and the Peltier module or between the Peltier module and the heat dissipation element is polished at about 10 micron or better.

6. The cryoprobe according to claim 1, wherein at least one contact surface between the cooling head and the Peltier module or between the Peltier module and the heat dissipation element is provided with a thermally conductive paste or a thermally conductive glue.

7. The cryoprobe according to claim 1, wherein said heat dissipation element is disk-like and is provided with a recess with a circular O-ring for sealing the cooling liquid and the Peltier module.

8. The cryoprobe according to claim 1, including a housing for containing said Peltier module, wherein said cooling head is provided with a recess having a circular O-ring for a thermal isolation between said cooling head and said housing.

9. The cryoprobe according to claim 1, comprising an electrical power supply coupled to said Peltier module and a temperature sensor thermally coupled to said cooling head, wherein said temperature sensor and the electrical power supply are coupled to an electronic control unit.

10. The cryoprobe according to claim 9, comprising means to program the temperature of said cooling head as a function of time under control of said temperature sensor.

11. The cryoprobe according to claim 1, wherein the Peltier module, cooling head, heat dissipation element, and the reservoir are enclosed in a thermally insulating housing.

12. The cryoprobe according to claim 11, wherein the cooling head protrudes from the thermally insulating housing.

13. The cryoprobe according to claim 1, further including an inlet for supplying the thermally conductive liquid to the reservoir, and an outlet for removing the thermally conductive liquid from the reservoir.

14. The cryoprobe according to claim 1, further including a mounting system for urging the cooling head, the Peltier module, and the heat dissipation element together to enhance thermal transfer.

15. The cryoprobe according to claim 14, wherein the mounting system galvanically isolates the cooling head from the thermally conductive liquid in the reservoir.

16. The cryoprobe according to claim 1, wherein the heat dissipation unit includes at least one cooling fin.

17. The cryoprobe according to claim 1, further including a temperature sensor located in the reservoir.

18. The cryoprobe according to claim 1, wherein the cooling head comprises a truncated cone having a slightly spherical surface.

19. The cryoprobe according to claim 1, further including a system for controlling current supplied to the Peltier module.

20. A cryoprobe comprising:

a Peltier module with a cold side and a hot side;

a system for supplying electrical energy to said Peltier module;

a cooling head thermally coupled to the cold side of the Peltier module;

a heat dissipation element thermally coupled to the hot side of the Peltier module; and a reservoir for a thermally conductive liquid thermally coupled to the heat dissipation element, the reservoir including an inlet for supplying the thermally conductive liquid to the reservoir, and an outlet for removing the thermally conductive liquid from the reservoir.

* * * * *